(12) United States Patent
Roby et al.

(10) Patent No.: US 7,967,134 B2
(45) Date of Patent: *Jun. 28, 2011

(54) SUTURE PLEDGET PACKAGE

(75) Inventors: Mark Roby, Killingworth, CT (US); John Kennedy, Guilford, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/407,503

(22) Filed: Mar. 19, 2009

(65) Prior Publication Data
US 2009/0230002 A1 Sep. 17, 2009

Related U.S. Application Data

(63) Continuation of application No. 11/602,658, filed on Nov. 21, 2006, now Pat. No. 7,520,383, which is a continuation of application No. 10/620,134, filed on Jul. 15, 2003, now Pat. No. 7,137,507.

(60) Provisional application No. 60/396,942, filed on Jul. 17, 2002.

(51) Int. Cl.
*A61B 17/06* (2006.01)

(52) U.S. Cl. .......................... 206/63.3; 206/227; 206/382

(58) Field of Classification Search .................. 206/63.3, 206/227, 340, 382; 606/232
See application file for complete search history.

(56) References Cited

U.S. PATENT DOCUMENTS

| | | |
|---|---|---|
| 3,136,418 A | 6/1964 | Stacy et al. |
| 3,162,307 A | 12/1964 | Regan, Jr. |
| 3,206,018 A | 9/1965 | Lewis et al. |
| 3,280,971 A | 10/1966 | Regan, Jr. |
| 3,338,019 A | 8/1967 | Trewella et al. |
| 3,338,401 A | 8/1967 | Regan, Jr. |
| 3,363,751 A | 1/1968 | Shave et al. |
| 3,444,994 A | 5/1969 | Kaepernik et al. |
| 3,487,917 A | 1/1970 | Shave et al. |
| 3,490,192 A | 1/1970 | Regan, Jr. |
| 3,545,608 A | 12/1970 | Berger |
| 3,613,879 A | 10/1971 | Kemble |
| 3,627,120 A | 12/1971 | Bordeau |
| 3,696,920 A | 10/1972 | Lahay |
| 3,759,376 A | 9/1973 | Lisowski |
| 3,779,375 A | 12/1973 | Foster |

(Continued)

FOREIGN PATENT DOCUMENTS

DE 3027836 3/1982

(Continued)

OTHER PUBLICATIONS

European Search Report for EP 03765545.3-2310 date of completion is Jul. 13, 2010 (3 pages).

*Primary Examiner* — Bryon P Gehman

(57) ABSTRACT

A suture pledget assembly is disclosed that includes a block with at least one slit and a pledget in an abutting relationship to the block. A suture has first and second end portions that are retained by the first and second slits, respectively. The first and second end portions generally extend beyond a face of the block and are substantially parallel to each other. A suture pledget package for retaining a suture is disclosed. The suture pledget package includes a front panel and a backing panel where the backing panel forms a plurality of tracks. Each track is configured and dimensioned to receive at least one suture pledget assembly.

5 Claims, 3 Drawing Sheets

U.S. PATENT DOCUMENTS

| | | | |
|---|---|---|---|
| 3,819,039 A | 6/1974 | Erickson |
| 3,857,484 A | 12/1974 | Thyen |
| 3,939,969 A | 2/1976 | Miller et al. |
| 3,972,418 A | 8/1976 | Schuler et al. |
| 3,985,227 A | 10/1976 | Thyen et al. |
| 4,034,850 A | 7/1977 | Mandel et al. |
| 4,063,638 A | 12/1977 | Marwood |
| 4,089,409 A | 5/1978 | Cerwin |
| 4,120,395 A | 10/1978 | Mandel et al. |
| 4,126,221 A | 11/1978 | Cerwin |
| 4,135,623 A | 1/1979 | Thyen |
| 4,183,431 A | 1/1980 | Schmidt et al. |
| 4,249,656 A | 2/1981 | Cerwin et al. |
| 4,253,563 A | 3/1981 | Komarnycky |
| 4,284,194 A | 8/1981 | Flatau |
| D263,505 S | 3/1982 | Black |
| 4,369,880 A | 1/1983 | Giggey et al. |
| 4,391,365 A | 7/1983 | Batchelor |
| 4,406,363 A | 9/1983 | Aday |
| 4,412,613 A | 11/1983 | Kibas |
| 4,412,614 A | 11/1983 | Ivanov et al. |
| 4,424,898 A | 1/1984 | Thyen et al. |
| 4,427,109 A | 1/1984 | Roshdy |
| D272,600 S | 2/1984 | Kubas |
| 4,496,045 A | 1/1985 | Ferguson et al. |
| 4,533,041 A | 8/1985 | Aday et al. |
| 4,549,649 A | 10/1985 | Roshdy |
| 4,555,016 A | 11/1985 | Aday et al. |
| 4,572,363 A | 2/1986 | Alpern |
| 4,573,575 A | 3/1986 | Bergrath et al. |
| 4,574,948 A | 3/1986 | Huck et al. |
| 4,574,957 A | 3/1986 | Stead |
| 4,615,435 A | 10/1986 | Alpern et al. |
| 4,699,271 A | 10/1987 | Lincoln et al. |
| 4,700,833 A | 10/1987 | Smith |
| 4,708,241 A | 11/1987 | Black |
| 4,813,537 A | 3/1989 | Okuhara et al. |
| 4,823,794 A | 4/1989 | Pierce |
| 4,896,767 A | 1/1990 | Pinheiro |
| 4,946,043 A | 8/1990 | Roshdy et al. |
| 4,961,498 A * | 10/1990 | Kalinski et al. ............ 206/63.3 |
| 5,099,994 A * | 3/1992 | Kalinski et al. ............ 206/63.3 |
| 5,123,528 A | 6/1992 | Brown et al. |
| 5,307,924 A | 5/1994 | Manosalva et al. |
| 5,348,146 A | 9/1994 | Sterling et al. |
| 5,566,822 A * | 10/1996 | Scanlon .................... 206/63.3 |
| 5,582,288 A | 12/1996 | Zatarga |
| 5,733,308 A | 3/1998 | Daugherty et al. |
| 5,769,214 A | 6/1998 | Zatarga |
| 5,919,208 A | 7/1999 | Valenti |
| 6,015,042 A * | 1/2000 | Cerwin et al. ............... 206/63.3 |
| 6,029,806 A | 2/2000 | Cerwin et al. |
| 6,138,440 A | 10/2000 | Gemma |
| 6,227,365 B1 | 5/2001 | Gary |
| 6,739,450 B2 | 5/2004 | Roshdy et al. |
| 6,938,755 B2 | 9/2005 | Braginsky et al. |
| 2004/0020795 A1 | 2/2004 | Braginsly et al. |

FOREIGN PATENT DOCUMENTS

| | | |
|---|---|---|
| FR | 2331638 | 6/1977 |
| FR | 2455880 | 12/1980 |
| GB | 680089 | 12/1952 |
| GB | 2148232 | 5/1985 |
| GB | 2161130 | 1/1986 |
| NL | 6504467 | 10/1966 |
| NL | 7302081 | 8/1973 |
| WO | WO 89/07420 A1 | 8/1989 |

* cited by examiner

SUTURE PLEDGET PACKAGE

CROSS-REFERENCE TO RELATED APPLICATIONS

This application is a continuation of U.S. application Ser. No. 11/602,658 filed Nov. 21, 2006, now U.S. Pat. No. 7,520,383, which is a continuation of U.S. application No. 10/620,134 filed Jul. 15, 2003, now U.S. Pat. No. 7,137,507, which claims priority of U.S. Provisional Application No. 60/396,942, filed Jul. 17, 2002, and the disclosures of each of the above-identified applications are hereby incorporated by reference in their entirety.

TECHNICAL FIELD

The present disclosure relates to a device for retaining a suture. More particularly, the present disclosure relates to a suture pledget assembly for retaining a suture in a predetermined spatial relationship to the pledget.

BACKGROUND OF RELATED ART

The use of pledgets in combination with sutures is known. Packages for suture and pledget combinations are also known. An example of a package for retaining surgical devices is disclosed in commonly owned U.S. Pat. No. 5,123,528, the contents of which are hereby incorporated by reference in their entirety. Pledgets are generally small buttressing pads used in conjunction with sutures to disperse the suture's holding force over a larger surface area.

It is an object of the present disclosure to provide a suture pledget assembly for retaining a suture in a predetermined spatial relationship to the pledget.

SUMMARY

This disclosure is directed towards an apparatus for fixating a suture in a predetermined position relative to a pledget. A block is positioned in operative association with the suture and pledget. The block includes at least one slit extending therethrough where the at least one slit is configured and adapted to engage at least a portion of the suture. The at least one slit is configured and dimensioned to maintain a substantially parallel relationship between first and second end portions of the suture. The block may be formed from foam.

This disclosure is also directed towards a suture pledget assembly including an elongated suture having a first end portion, a second end portion, and an intermediate portion therebetween. The suture pledget assembly further includes a block having at least one slit extending therethrough where the at least one slit is configured and adapted to engage at least a portion of the suture. A pledget is included that has a front wall preferably in an abutting relation to the block such that the front wall of the pledget is substantially flush with the block. First and second end portions of the suture are held in the block substantially parallel to each other.

This disclosure is also directed towards a suture pledget package including a suture pledget assembly having an elongated suture and a block. The block includes at least one slit extending therethrough and is configured and adapted to engage at least a portion of the suture. The suture is disposed in the block such that first and second end portions of the suture extend beyond the block. The suture pledget package further includes a pledget having an intermediate portion of the suture disposed therein and where the intermediate portion is disposed between the at least one slit, and a package having a backing panel defining a plurality of elongated tracks where each track configured and dimensioned for receiving at least one suture pledget assembly, and a front panel attached to the backing panel.

BRIEF DESCRIPTION OF THE DRAWINGS

Preferred embodiments of the presently disclosed suture pledget package are described herein with reference to the drawings, wherein.

DETAILED DESCRIPTION OF THE PREFERRED EMBODIMENTS

Figure 2:
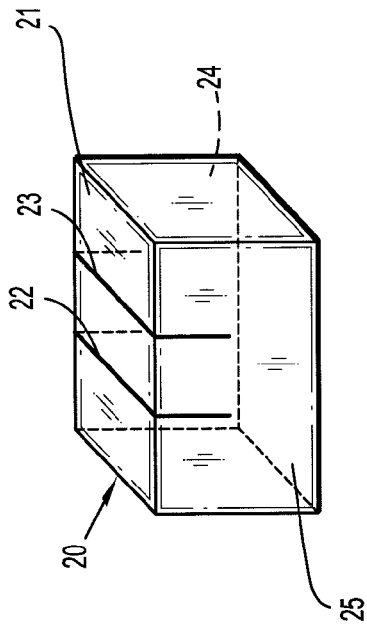
FIG. 2 is a perspective view of a block having first and second slits according to an embodiment of the present disclosure.

Preferred embodiments of the presently disclosed suture pledget package will now be described in detail with reference to the drawings, in which like reference numerals and characters designate identical or corresponding elements in each of the several views. As used herein, the term "distal" refers to that portion of the tool, or component thereof which is further from the user while the term "proximal" refers to that portion of the tool or component thereof which is closer to the user.

Figure 1:
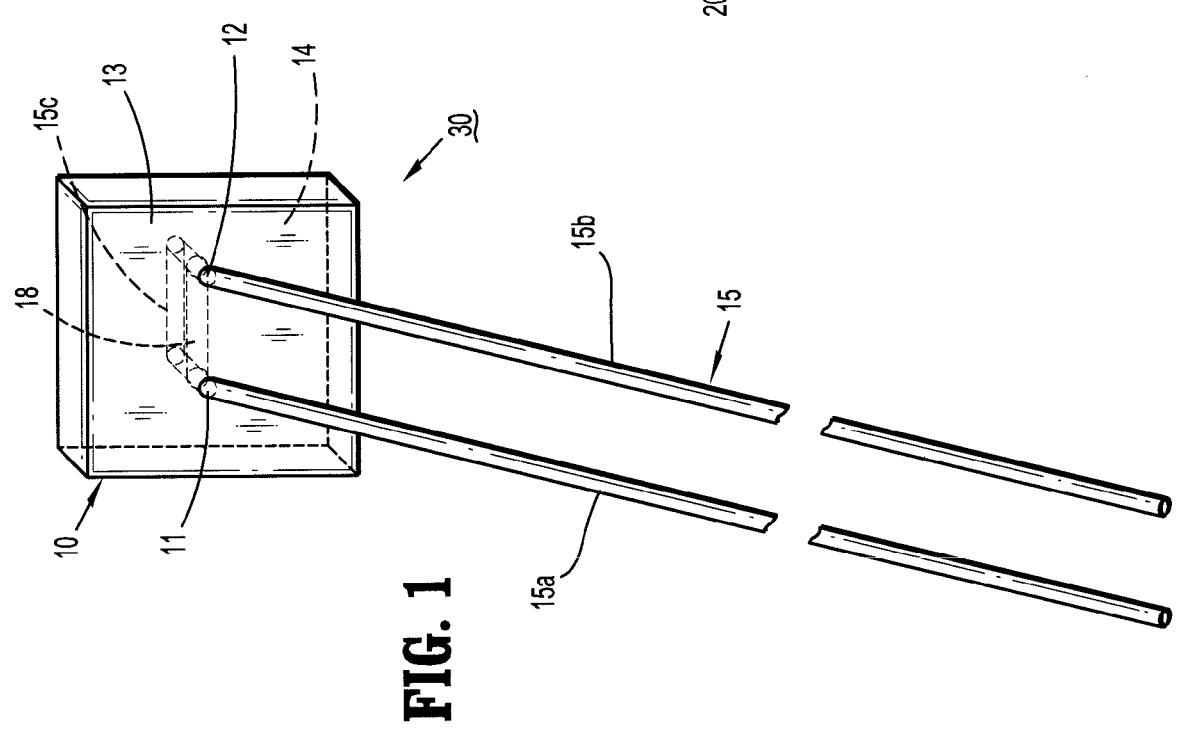
FIG. 1 is perspective view of a pledget assembly according to an embodiment of the present disclosure.

With reference to FIG. 1, there is illustrated a pledget assembly 30 including a pledget 10 and a suture 15. Pledget 10 is pad of material having a generally rectangular shape with front and rear surfaces 13, 14. Pledget 10 is formed from a suitable biocompatible material as is known in the art and preferably from Teflon® that is marketed by DuPont Nemours, Wilmington, Del. Front and rear surfaces 13, 14 are of a generally planar configuration. A pair of generally circular openings 11 and 12 is disposed on front surface 13. Preferably, openings 11 and 12 extend from front surface 13 to rear surface 14, thereby forming passages through pledget 10. Additionally, each opening 11, 12 is configured and dimensioned for slidably receiving suture 15.

Suture 15 is an elongated structure that is generally cylindrical in shape. Although suture 15 is illustrated as a cylindrical structure in FIG. 1, alternative shapes, such as a rectangle or an ellipse, may be substituted for the cylindrical configuration without departing from the scope of the present disclosure. Suture 15 includes a first end portion 15a, a second end portion 15b, and an intermediate portion 15c disposed therebetween. Suture 15 is formed from a suitable bioabsorbable or biocompatible material such as cotton, nylon, or other suitable material for sutures as are known in the art.

In a preferred orientation for use, intermediate portion 15c of suture 15 is positioned against rear surface 14 of pledget 10 such that intermediate portion 15c is substantially flush against rear surface 14. In the alternative, pledget 10 can have a channel 18 internal to it for receiving intermediate portion 15c. Channel 18 is in communication with openings 11 and 12 to form a contiguous passageway for suture 15. First and second end portions 15a, 15b pass through first and second openings 11, 12 such that at least a portion of first and second end portions 15a, 15b extend beyond front surface 13. Additionally, when suture 15 is positioned in pledget 10 with intermediate portion 15c substantially flush against rear surface 14, first and second end portions 15a, 15b are substantially perpendicular in relationship to intermediate portion 15c as seen in FIG. 1. In a configuration that includes channel 18, intermediate portion 15c is disposed between openings 11 and 12 internal to pledget 10.

Referring now to FIG. 2, a block 20 having first and second slits 22 and 23 disposed on a top face 21 is shown. Block 20 is generally rectangular and includes opposing front and rear faces 24, 25 with top face 21 disposed therebetween. Top face, and front and rear faces 24, 25 are generally planar. Block 20 is formed from a foam material as is known in the art and preferably formed from a styrofoam material as disclosed in commonly owned U.S. Pat. No. 5,123,528.

More particularly, slits 22 and 23 extend from rear face 24 to front face 25 along top face 21. Additionally, each slit 22, 23 preferably extends below top face 21a predetermined amount defining the depth of slits 22 and 23, where the depth of each slit 22, 23 is substantially identical. It is preferred that slits 22 and 23 are substantially parallel to one another to maintain a substantially uniform distance between the slits 22 and 23. Both slits 22 and 23 are configured and dimensioned for receiving at least a portion of suture 15 where each slit 22, 23 is further configured and dimensioned for releasably retaining at least a portion of suture 15. By maintaining a substantially uniform distance between slits 22, 23, a substantially uniform distance is maintained between first and second end portions 15a, 15b when a suture 15 is inserted into block 20 (see FIG. 3)

Figure 2A:
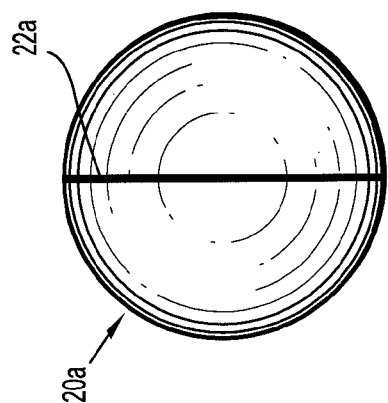
FIG. 2A is a perspective view of a block having at least one slit according to another embodiment of the present disclosure.

In an alternative embodiment as illustrated in FIG. 2A, block 20a is a generally spherical structure. Block 20a includes a slit 22a extending therethrough. Block 20a is formed from a foam material as is known in the art and preferably formed from a styrofoam material as disclosed in commonly owned U.S. Pat. No. 5,123,528. As in the previously discussed embodiment, slit 22a preferably extends into block 20a a predetermined amount defining the depth of slit 22a. Slit 22a is configured and dimensioned for receiving at least a portion of suture 15 where slit 22a is further configured and dimensioned for releasably retaining at least a portion of suture 15.

Although the block has been illustrated as a generally rectangular (FIG. 2) or spherical (FIG. 2A) structure, it is contemplated and appreciated that the block may be formed in other shapes that maintain the predetermined suture/pledget spatial orientation. Examples of other shapes include ellipses, ovals, etc.

Figure 3:
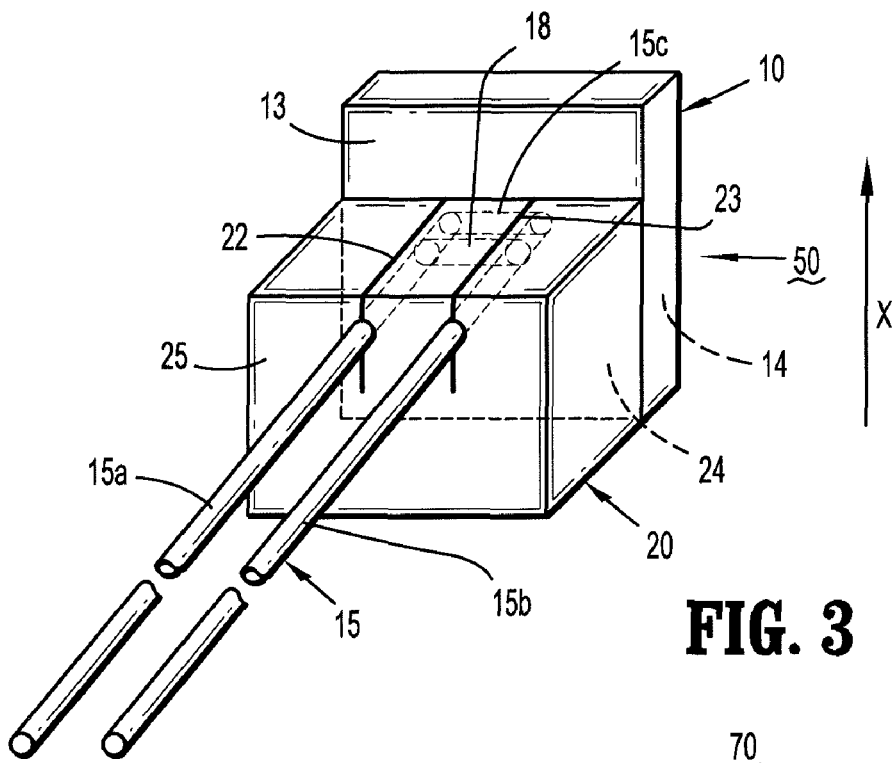
FIG. 3 is a perspective view of a suture pledget assembly according to an embodiment of the present disclosure.

Referring now to FIG. 3, a suture pledget assembly 50 is illustrated. According to an embodiment of the present disclosure, suture pledget assembly 50 includes pledget 10, suture 15, and block 20. Advantageously, pledget 10 and suture 15 are combined to form pledget assembly 30 as previously discussed. Block 20, as previously discussed, includes slits 22, 23 that are adapted to receive at least a portion of first and second end portions 15a, 15b of suture 15. By combining block 20 with pledget assembly 30, at least a portion of first and second end portions 15a, 15b are releasably captured by slits 22 and 23. As shown in FIG. 3, slits 22, 23 maintain a substantially uniform distance between first and second end portions 15a, 15b since slits 22, 23 are substantially parallel to one another. Preferably, slits 22 and 23 are perpendicular to front face 25 and rear face 24 of block 20 and extend below top surface 21a predetermined distance, or depth where the depth of slit 22 is substantially identical to the depth of slit 23. It is desirable for slits 22 and 23 to have sufficient depth to accommodate suture 15 while providing sufficient distance between suture 15 and top surface 21 for slits 22 and 23 to return to a first state, as discussed in detail below.

Advantageously, block 20 is formed from a resilient foam material where slits 22 and 23 are biased by the foam material into a first, or closed state. In the first state, slits 22, 23 are configured to retain first and second end portions 15a, 15b of suture 15 where the bias of the foam material exerts a biasing force laterally against slits 22, 23 to close slits 22, 23 along top surface 21. In the region surrounding at least a portion of first and second end portions 15a, 15b, the bias of the foam material exerts the biasing force laterally against slits 22, 23 for capturing and retaining suture 15, and particularly capturing and retaining at least a portion of first and second end portions 15a, 15b within block 20. By applying a force to overcome the bias of the foam material, slits 22, 23 are moved into a second or open state where they are configured to receive at least a portion of first and second end portions 15a, 15b. Once the force is removed, the bias of the foam material applies the biasing force to move slits 22, 23 into the first state.

In an exemplary configuration, first and second end portions 15a, 15b of pledget assembly 30 are inserted into slits 22, 23 by overcoming the bias of the foam material. Once the suture is placed in a desired position within block 20, the force is removed allowing the biasing force of the foam material to move slits 22, 23 into the first state, thereby capturing and retaining suture 15 within block 20. Preferably, pledget assembly 30 is attached to block 20 such that front surface 13 of pledget 10 is in an abutting relationship with rear face 24 of block 20. It is further preferred that front surface 13 is positioned substantially flush with rear face 24 to minimize undesired movement of suture 15 and maintain a perpendicular relationship between first and second end portions 15a, 15b and front surface 13. By forming suture pledget assembly 50 as discussed above, suture 15 and particularly first and second end portions 15a, 15b, are captured and retained in a predetermined spatial relationship to pledget 10. More particularly, first and second end portions 15a, 15b are maintained in a perpendicular relationship to front surface 13.

Figure 4:
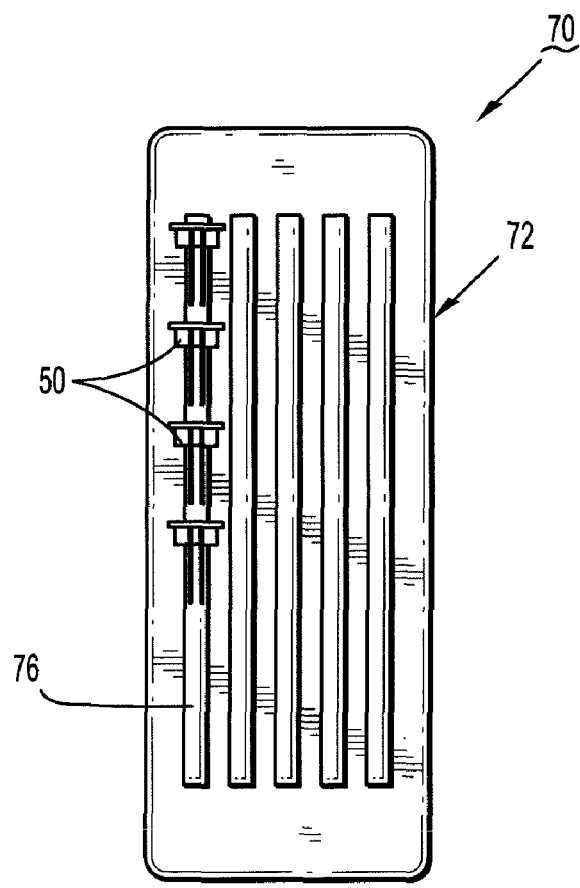
FIG. 4 is front view of a package without a front panel including a plurality of suture pledget assemblies according to an embodiment of the present disclosure.
Figure 5:
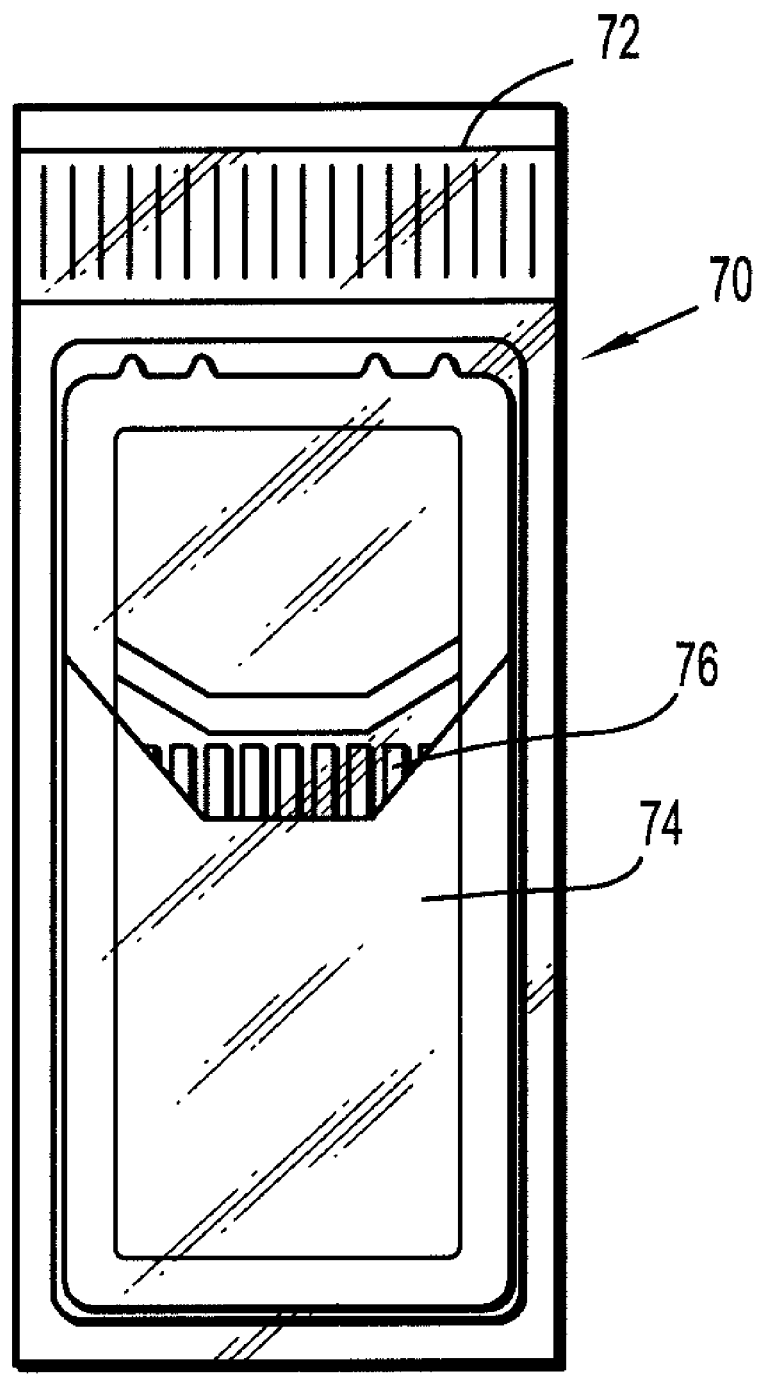
FIG. 5 is a front view of the package of FIG. 4 including the front panel.

Referring now to FIGS. 4 and 5, another embodiment of the present disclosure is illustrated. As shown in FIGS. 4 and 5, a package 70 includes a backing panel 72 and a front, or protective panel 74. Package 70 is a generally rectangular shape having a number of elongated tracks 76 that are longitudinally oriented in and/or on backing panel 72. Each track is configured and dimensioned to receive a number of suture pledget assemblies 50. Additionally, each track 76 includes an adhesive suitable for retaining each suture pledget assembly 50 in position. Tracks 76 may be formed integrally with backing panel 72 as raised or recessed tracks. Alternately, tracks 76 may be strips of material that are fixedly attached to backing panel 72 in a longitudinal orientation. Tracks 76 are substantially parallel to one another and are positioned in package 70 to define a gap 77 between each pair of tracks 76.

In FIG. 5, package 70 is shown with front panel 74 attached to backing panel 72. Once the panels are attached, suture pledget assemblies 50 are contained within package 70 where package 70 acts to minimize physical trauma to suture pledget assemblies 50 and further minimize biological contamination of suture pledget assemblies 50 as discussed below. Package 70 is formed from surgical Kraft paper, aluminum, or other suitable packaging materials as are known in the art.

In a preferred embodiment, backing panel 72 is formed from a polymer such as polyolefin (i.e. TYVEK®) as disclosed in U.S. Pat. No. 6,138,440, the contents of which are hereby incorporated by reference in their entirety. Package 70 and its contents can be sterilized by various methods such as gamma radiation and gaseous sterilization with steam or ethylene oxide. In the event that gaseous sterilization is employed, at least portion of backing panel 72 should be fabricated from a porous microbe-impervious material such as TYVEK® brand spun bonded polyolefin sheet as marketed by DuPont DeNemours, Wilmington, Del. Such methods of sterilization are known to those with skill in the art. Additionally, front panel 74 may be formed from a material such that has at least a portion of front panel 74 is substantially transparent for allowing the practitioner to view the contents of package 70 prior to opening it.

Removal of a single pledget assembly 30 is hereinafter discussed with the principles being applicable to removal of multiple pledget assemblies 30. The practitioner obtains package 70 including a number of suture pledget assemblies 50 from a storage area and separates front panel 74 from package 70 to expose backing panel 72 with suture pledget assemblies 50. Suture pledget assemblies 50 are attached to tracks 76 by a suitable adhesive. As the practitioner removes a pledget assembly 30 from package 70 by applying a removal force to pledget 10 in the direction of arrow-X, the removal force overcomes the biasing force of the foam material in block 20. This causes suture 15, and particularly first and second end portions 15a, 15b to move in the direction of the removal force and causing slits 22, 23 to move into the first state. As slits 22, 23 move into the first state, the practitioner separates pledget assembly 30 from block 20. More specifically, by separating pledget assembly 30 from block 20, the practitioner separates, or removes suture 15 from block 20. Therefore first and second end portions 15a, 15b are separated from first and second slits 22, 23 respectively. Block 20 is retained in track 76 by the adhesive material applied to track 76 as pledget assembly 30 is removed from package 70.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A suture package comprising:
   at least one block including at least one slit extending therethrough;
   at least one suture, at least a portion of the at least one suture is received within the at least one slit of the at least one block;
   a backing panel defining a plurality of elongated tracks, each elongated track receiving the at least one block and the at least one suture, and a front panel attached to the backing panel.

2. The package of claim 1, wherein the at least one block includes two said slits.

3. The package of claim 1, further comprising an adhesive material for retaining the at least one block in the plurality of elongated tracks.

4. The package of claim 1, wherein the at least one block includes a first face, a second face, and a top face therebetween.

5. The package of claim 1, wherein the at least one block is a generally spherical structure.

* * * * *